(12) United States Patent
Loy

(10) Patent No.: US 9,457,114 B2
(45) Date of Patent: Oct. 4, 2016

(54) APPARATUS AND METHOD FOR STERILIZING CONTAINERS

(71) Applicant: KRONES AG, Neutraubling (DE)

(72) Inventor: Michael Loy, Regensburg (DE)

(73) Assignee: KRONES, AG, Neutraubling (DE)

( * ) Notice: Subject to any disclaimer, the term of this patent is extended or adjusted under 35 U.S.C. 154(b) by 0 days.

(21) Appl. No.: 14/107,505

(22) Filed: Dec. 16, 2013

(65) Prior Publication Data

US 2014/0178250 A1 Jun. 26, 2014

(30) Foreign Application Priority Data

Dec. 20, 2012 (DE) .................. 10 2012 112 803

(51) Int. Cl.
| | |
|---|---|
| A61L 2/26 | (2006.01) |
| B08B 9/28 | (2006.01) |
| B08B 9/34 | (2006.01) |
| A61L 2/16 | (2006.01) |
| B29C 49/42 | (2006.01) |
| A61L 2/20 | (2006.01) |
| B29C 49/06 | (2006.01) |

(52) U.S. Cl.
CPC .. *A61L 2/26* (2013.01); *A61L 2/16* (2013.01); *A61L 2/20* (2013.01); *B08B 9/283* (2013.01); *B08B 9/34* (2013.01); *B29C 49/4252* (2013.01); *A61L 2202/23* (2013.01); *B29C 49/06* (2013.01)

(58) Field of Classification Search
CPC .................................. A61L 2/16; A61L 2/26
USPC ................................................ 422/28, 292
See application file for complete search history.

(56) References Cited

U.S. PATENT DOCUMENTS

| | | | |
|---|---|---|---|
| 4,102,351 A | * | 7/1978 | Wiendahl et al. ............ 134/129 |
| 8,453,419 B2 | | 6/2013 | Roithmeier et al. |
| 2008/0152538 A1 | | 6/2008 | Quetel et al. |
| 2011/0061343 A1 | | 3/2011 | Roithmeier et al. |
| 2012/0048683 A1 | | 3/2012 | Forsthoevel et al. |

(Continued)

FOREIGN PATENT DOCUMENTS

| | | |
|---|---|---|
| CN | 101219229 | 7/2008 |
| CN | 102019686 | 4/2011 |
| DE | 102007050582 | 10/2007 |

(Continued)

OTHER PUBLICATIONS

Machine translation of DE 102008038143; published Feb. 2010; Engelhard et al.*

(Continued)

*Primary Examiner* — Sean E Conley
(74) *Attorney, Agent, or Firm* — Onello & Mello, LLP

(57) ABSTRACT

An apparatus for sterilizing plastic preforms, comprises a transport device that transports the plastic preforms along a predefined transport path, each plastic preform extending in a longitudinal direction; and a plurality of actuation devices. Each actuation device inputs a flowable medium into interiors of the plastic preforms, respectively. The actuation devices travel with the plastic preforms in a transport direction along the transport device. The actuation devices at least one of inject the flowable medium into the plastic preforms at a predefined angle α relative to the longitudinal directions of the plastic preforms, or include longitudinal directions, respectively, that are offset relative to the longitudinal directions of the plastic preforms.

25 Claims, 2 Drawing Sheets

(56) References Cited

U.S. PATENT DOCUMENTS

2012/0260955 A1    10/2012    Winzinger
2013/0183195 A1    7/2013    Herold et al.

FOREIGN PATENT DOCUMENTS

| | | | |
|---|---|---|---|
| DE | 102008038143 | * | 2/2010 |
| DE | 102010032336 | | 7/2010 |
| DE | 102010035496 | | 3/2012 |
| DE | 102010056450 | | 6/2012 |
| DE | 102011007280 | | 10/2012 |
| EP | 2295324 | | 3/2011 |
| WO | 2009052800 | | 4/2009 |
| WO | 2012010166 | | 1/2012 |

OTHER PUBLICATIONS

Machine translation of DE 102010032336; published Jan. 2012; Herold et al.*

Extended European Search Report dated Mar. 20, 2014 issued in corresponding European Application No. 13199199.4.

China Office Action dated Jun. 30, 2015 issued in corresponding Application No. 2013106894978.

\* cited by examiner

APPARATUS AND METHOD FOR STERILIZING CONTAINERS

CROSS-REFERENCE TO RELATED APPLICATION

This application claims priority to German Patent Application No. 10 2012 112 803.0, filed Dec. 20, 2012, in the German Patent and Trademark Office the content of which is incorporated herein by reference, in its entirety.

FIELD

The present inventive concepts relate to an apparatus and a method for sterilizing containers, and in particular the sterilizing or respectively cleaning of plastic preforms.

BACKGROUND

In the drinks-producing industry, it is known that plastic containers are sterilized prior to filling. During a sterilization process, both an inner surface of the plastic containers and an outer surface can be sterilized. Sterilization can take place by germicidal irradiation, such as for example beta radiation. Sterilization can also occur by the application of a sterilization agent, such as a hydrogen peroxide gas. However, when forming plastic containers, conventional processes including the sterilization of not only the finished plastic containers, but also the preforms themselves. In this manner, a certain pre-sterilization of the plastic preforms can be achieved before they are expanded into plastic containers.

SUMMARY

Example embodiments will be more clearly understood from the following detailed description taken in conjunction with the accompanying drawings. The drawings herein represent non-limiting, example embodiments as described herein.

In an aspect, provided is an apparatus for sterilizing plastic preforms, comprising: a transport device that transports the plastic preforms along a predefined transport path, each plastic preform extending in a longitudinal direction; and a plurality of actuation devices, each actuation device inputting a flowable medium into interiors of the plastic preforms, respectively, wherein the actuation devices travel with the plastic preforms in a transport direction along the transport device, and wherein the actuation devices at least one of inject the flowable medium into the plastic preforms at a predefined angle α relative to the longitudinal directions of the plastic preforms, or include longitudinal directions, respectively, that are offset relative to the longitudinal directions of the plastic preforms.

In some embodiments, the actuation devices inject the flowable medium into the plastic preforms at the predefined angle α, and a longitudinal direction of actuation device of the actuation devices is offset from a longitudinal direction of a plastic preform of the plastic preforms by a predetermined distance.

In some embodiments, wherein the actuation devices are arranged such that they inject the flowable medium into the plastic preforms at the predefined angle α that is different from 0° along which the longitudinal direction of the plastic preforms extend, such that a direction of injection has a component which is oriented opposite to the transport direction of the plastic preforms.

In some embodiments, the longitudinal direction of an actuation device of the actuation devices in a direction of movement of the plastic preforms is offset in relation to the longitudinal directions of the plastic preforms with respect to the transport direction of the plastic preforms.

In some embodiments, the apparatus further comprises a gap between mouths of the plastic preforms and the actuation devices, the gap extending in the transport direction of the plastic preforms.

In some embodiments, the actuation devices are arranged on a carrier.

In some embodiments, the predefined angle α is between 5° and 50°. In some embodiments, the predefined angle α is between 10° and 30°. In some embodiments, the predefined angle α is between 10° and 20°. In some embodiments, the predefined angle α is between 12° and 18°.

In some embodiments, the distance between the longitudinal direction of the plastic preforms and the longitudinal direction of the actuation devices is between 2 mm and 12 mm. In some embodiments, the distance between the longitudinal direction of the plastic preforms and the longitudinal direction of the actuation devices is between 4 mm and 10 mm. In some embodiments, the distance between the longitudinal direction of the plastic preforms and the longitudinal direction of the actuation devices is between 5 mm and 9 mm.

In some embodiments, at least one of the predefined angle, the offset between the longitudinal direction of the plastic preforms and longitudinal directions of the actuation devices, or a height of the gap between the plastic preforms and the actuation device is adjustable.

In some embodiments, the apparatus further comprises a deflection device which deflects a sterilization agent emerging from a plastic container of the plastic preforms onto an outer region of the plastic container.

In some embodiments, a carrier is arranged adjacent to the mouth of the plastic preforms, wherein the carrier has at least one recess on a mouth of a plastic container of the plastic preforms which recess extends beyond a mouth edge of the plastic container in a radial direction thereof.

In another aspect, a method for sterilizing plastic preforms, comprises transporting the plastic preforms along a predefined path; and during the transporting of the plastic preforms, actuating an interior of the plastic preforms by inputting a flowable sterilization agent into the interior from a plurality of actuation devices. The actuation devices at least one of inject the flowable sterilization agent into the plastic preforms at a predefined angle α relative to the longitudinal directions of the plastic preforms, or include longitudinal directions, respectively, that are offset relative to the longitudinal directions of the plastic preforms.

In some embodiments, the actuation devices are arranged such that they inject the flowable medium into the plastic preforms at the predefined angle α that is different from 0° along which the longitudinal direction of the plastic preforms extend, such that a direction of injection has a component which is oriented opposite to the transport direction of the plastic preforms.

In some embodiments, the longitudinal direction of an actuation device of the actuation devices in a direction of movement of the plastic preforms is offset in relation to the longitudinal directions of the plastic preforms with respect to the transport direction of the plastic preforms.

In some embodiments, the method further comprises forming a gap between mouths of the plastic preforms and the actuation devices, the gap extending in the transport direction of the plastic preforms.

DETAILED DESCRIPTION

Figure 1:
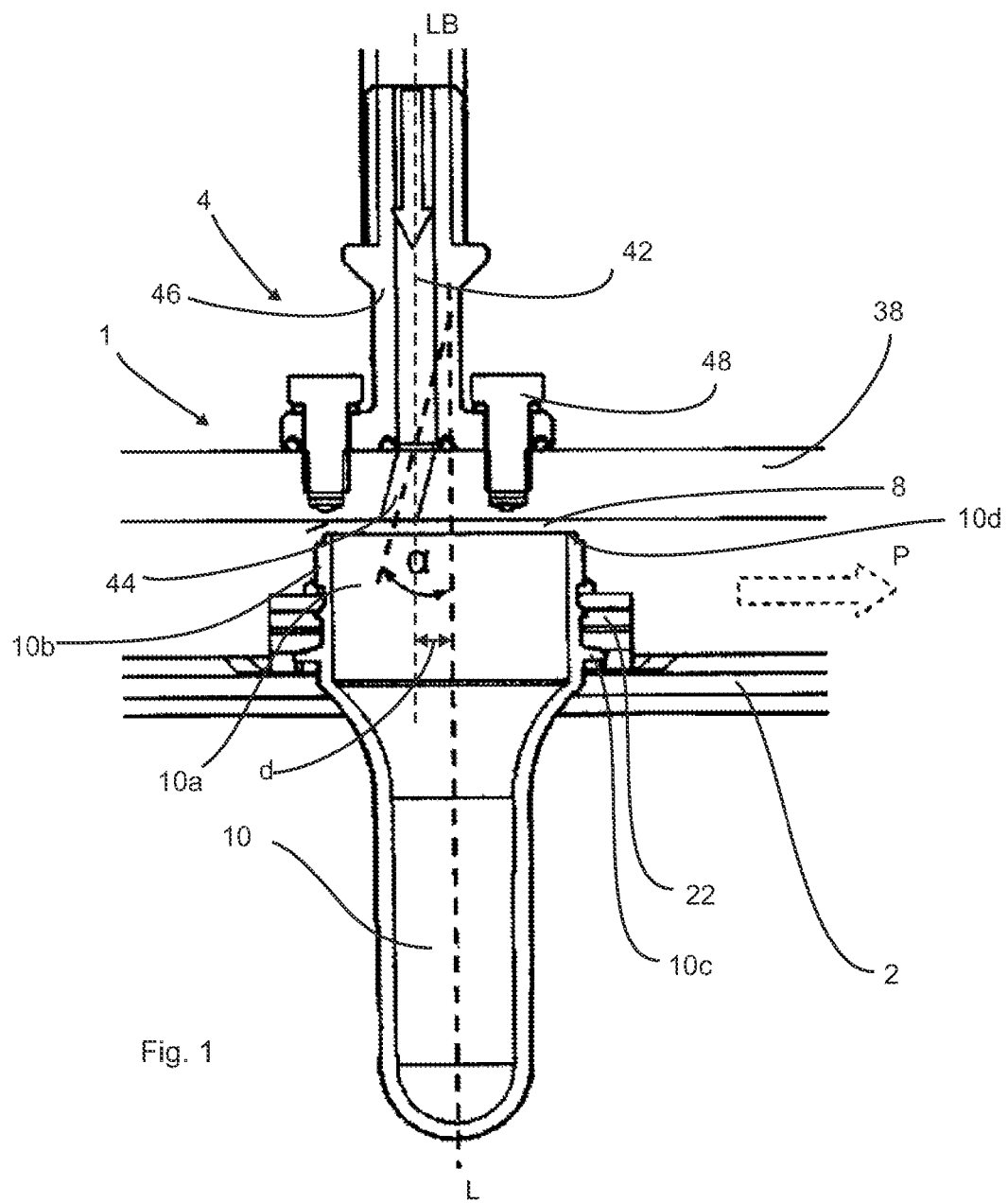
FIG. 1 is a diagrammatic view of an apparatus for sterilizing plastic preforms, in accordance with some embodiments.

To improve the conservability of sensitive filling products with respect to polyethylene terephthalate (PET) containers or the like, before the filling process is performed, it is preferred that the number of germs or other undesirable contaminants on the containers be substantially reduced. Various wet and dry aseptic methods are known for achieving this at least in part. However, because of the sometimes large bottle volumes, a high consumption of sterilization agent such as peracetic acid or hydrogen peroxide may be required. More recent machine designs therefore can reduce the number of germs in the plastic preform before the bottles are blown. Thereby, the plastic preform passes through a treatment region in which it is disinfected by gaseous or liquid sterilization agents or by irradiation, for example irradiation with ultraviolet radiation or electron actuation. To make the treatment region small and cost-efficient, it is advantageous that the containers to be sterilized are completely covered with the respective sterilization agent as quickly as possible. In particular, in the case of fluidic sterilization agents, the design and arrangement of the corresponding injection nozzle, which introduces the sterilization agent into the containers, play a decisive role.

Embodiments of the present inventive concepts include systems, devices, and methods that relate to improving the sterilization of plastic containers, in particular by the actuation with a flowable medium.

An apparatus according to some embodiments for cleaning and/or sterilizing plastic preforms includes a transport device, which transports the plastic preforms along a predefined transport path. Furthermore the apparatus has a plurality of actuation devices which actuate upon the plastic preforms with a flowable sterilization agent, and in particular, a gaseous sterilization agent.

According to some embodiments, the actuation device is formed movably together with the plastic preforms, wherein the actuation devices are arranged such that they can inject the flowable medium into the plastic preforms at a predefined angle different from 0° to the longitudinal direction thereof, and/or the longitudinal directions of the actuation devices are arranged to be offset relative to the longitudinal directions of the plastic preforms. According to some embodiments of the inventive concepts, the arrangement of the actuation devices is modified in relation to the obvious central arrangement and the corresponding rectilinear injection of the sterilization agent into the containers.

As shown below in detail, with the arrangement of the actuation devices according to the inventive concepts, a more effective distribution of the sterilization agent in the interior of the plastic preforms is achieved. However, advantageously, the actuation devices are arranged such that the sterilization agent emerging therefrom is introduced into the plastic preforms substantially and preferably completely via their mouths. In this way the apparatus according to the inventive concepts can sterilize the inner surfaces of the plastic preforms. The plurality of actuation devices is advantageously arranged on a movable carrier, and more particularly, transported along a closed transport path.

In some embodiments, the movable carrier is a rotatable carrier, and in particular, includes a sterilization wheel on which a plurality of said actuation devices is arranged. Advantageously, a plurality of holding devices is arranged on the carrier to hold the plastic preforms, wherein preferably an actuation device is allocated to each individual holding device. Accordingly, during the sterilization process, each actuation device is arranged in a precisely defined position in relation to the plastic preform or its holding device allocated to this actuation device, the position of which preferably does not change even during sterilization of the plastic preforms.

Stationary actuation devices are clearly distinguished from moving actuation devices, or nozzles. In the case of stationary actuation devices, the plastic preforms are transported past and below the nozzles for treatment. In this way, a relatively short injection time is available. With a continuous nozzle outflow, the majority of the sterilization agent is output to the intermediate spaces, whereby high losses are incurred. With a cyclic injection, a complex mechanical solution is necessary. By moving the actuation devices, conversely the time for actuation can be extended even for high transport rates of the plastic preforms. Preferably the actuation devices are arranged above the respective holding devices or respectively plastic preforms. During transport, i.e. during rotation of the rotatable carrier, the actuation devices are preferably guided in synchrony above the respective plastic preforms.

In other words, moving the actuation devices, or respectively, nozzles, with a continuous outflow can result in longer treatment times. By moving the actuation device and the plastic preform, however, a flow is formed in the intermediate gap which, as will be explained in more detail below, can have a disruptive influence on the optimum throughflow of plastic preforms when gaseous sterilization agents in particular are used. The present inventive concepts provide in particular for the sterilization of the plastic preforms with a gaseous sterilization agent. Thereby, both the plastic preform and the actuation device are moved in the transport direction. To minimize the disruptive influence of the resulting gap flow, the actuation device is angled relative to the transport direction by an angle $\alpha$ and/or advantageously offset eccentrically in relation to the centre of the plastic preform, and in particular offset eccentrically along the transport direction.

In a preferred embodiment, the actuation devices are arranged such that they inject the flowable medium into the plastic preforms at a predefined angle different than 0° in relation to the longitudinal direction thereof. A longitudinal direction of the actuation devices is arranged to be offset in relation to the longitudinal direction of the plastic preforms. Thus, embodiments include a combination of the measures described above, i.e. the oblique position of the actuation device and its offset in relation to the longitudinal direction of the plastic preforms. In this manner, a highly efficient injection of sterilization agent into the plastic preforms is achieved.

In a further advantageous embodiment, the actuation devices are arranged such that they inject the flowable sterilization or respectively cleaning agent into the plastic preforms at a predefined angle different from 0° in relation to the longitudinal direction thereof, preferably such that the injection direction also has a component which is oriented opposite the transport direction of the plastic preforms.

With this procedure, the injection can also take place with a component opposite the direction of movement of the plastic preforms. Here, the oblique position can be formed in a plane which also contains a direction of movement of the plastic preforms and a longitudinal direction of the plastic preforms to be sterilized.

In a further advantageous embodiment, a longitudinal direction of the actuation devices is in each case arranged behind the longitudinal directions of the plastic preforms, in the direction of movement of movement of the plastic preforms. In this embodiment, the individual actuation devices are offset to the rear in relation to their allocated plastic preforms or respectively in relation to the plastic preforms to be sterilized, in each case viewed in the transport direction of the plastic preforms. Thus, the actuation devices each trail their allocated plastic preforms in the direction of movement of the plastic preforms In a further advantageous embodiment, a gap which extends in the transport direction of the plastic preforms is formed between the mouths of the plastic preforms and the actuation devices. More precisely, this gap can be formed between a carrier of the actuation devices and the plastic preforms. This gap also serves to generate a flow which is guided through the plastic preforms for sterilization. The actuation devices can therefore protrude at least slightly into the mouths of the plastic preforms. Advantageously, the actuation devices or respectively the nozzles can be arranged above the mouth edges of the plastic preforms or respectively spaced from these mouth edges.

In some embodiments, the height of the gap is between 0.5 mm and 10 mm. In some embodiments, the gap height is between 1 mm and 8 mm. In some embodiments, the gap height is between 1 mm and 5 mm. In some embodiments, the gap height is between 1 mm and 3 mm.

In another embodiment, the actuation devices are arranged on a carrier. Thereby, the carrier is movable, and preferably also moves the plastic preforms. As stated above, in some embodiments, the carrier is circular and is rotated in relation to a rotational axis.

In some embodiments, the predefined angle at which the sterilization agent flows in is between 5° and 50°. In some embodiments, the predefined angle is between 10° and 30°. In some embodiments, the predefined angle between 10° and 20°. In some embodiments, the predefined angle between 12° and 18° in relation to the longitudinal direction of the plastic preforms. This angle ensures that a gaseous sterilization agent reaches as far as the base of the plastic preforms in a comparatively very short time and also, with correspondingly guided flow, emerges again from the plastic preforms. In this way, extensive wetting or respectively actuation of the inner walls of the plastic preform with the sterilization agent is possible.

In a further preferred embodiment, a distance d between the longitudinal direction of the plastic preforms and the longitudinal direction of the actuation devices is between 2 mm and 12 mm. In other embodiments, the distance d is between 4 mm and 10 mm. In other embodiments, the distance d is between 5 mm and 9 mm. However, this distance can also on the mouth cross-section of the plastic preforms to be sterilized. Advantageously the plastic preforms are transported in a vertical orientation, and preferably, the actuation devices are each arranged above their allocated plastic preforms.

In a further advantageous embodiment, the predefined angle and/or the offset between the longitudinal direction of the plastic preforms and the longitudinal directions of the actuation devices is adjustable. Preferably, these parameters are also variable. In a further preferred embodiment, the height of the gap above the mouths of the plastic preforms is also variable. Preferably, the gap height is also adjustable. In this manner, an adjustment to different plastic preform geometries can be achieved. Advantageously an adjustment device is provided, which allows a common or separate modification of the parameters of the individual actuation devices, where the foregoing can also be applicable automatically.

Thus, it is possible for the actuation devices to be arranged on a common carrier, which in turn is arranged rotationally movably in relation to another carrier on which the plastic preforms are arranged, so that the offset of the actuation devices can be modified uniformly. Furthermore, it is possible for the actuation devices to be arranged on two carriers which are rotatable in relation to each other, which also allows a common adjustment of the angles or respectively injection devices of all actuation devices.

In a further advantageous embodiment, the actuation devices have a bore diameter or respectively outlet diameter for the sterilization agent which is between 3 mm and 8 mm.

In general, the apparatus can include a deflection device which deflects the sterilization agent emerging again from the plastic container onto an outer region of the mouth of the plastic container.

In a further advantageous embodiment, a carrier is adjacent to the mouth of the plastic containers. This carrier has a recess at one of the mouths of the plastic containers. The recess extends beyond the mouth edge of the plastic container in a radial direction thereof. The sterilization agent emerging again from the plastic container can be deflected by this recess onto an outer face of the thread of the plastic container and thus sterilize it. Advantageously this recess has a curved profile which causes a corresponding deflection of the sterilization agent.

It is pointed out that this embodiment with the recess, or in general with the deflection device, can also be used independently of the embodiments of the actuation device or respective nozzle described above.

Advantageously said carrier is arranged above the plastic containers. In a further advantageous embodiment, the carrier has a protrusion pointing towards the plastic containers or respectively plastic preforms.

Thus, it is possible that a recess of such a type is provided which extends above the mouths of all plastic containers. Here, it is possible that a first such recess or respectively groove is provided which is arranged radially inside the longitudinal directions of the plastic containers in relation to their longitudinal directions. Preferably, a second groove is provided which is arranged outside the longitudinal directions of the plastic containers in relation to their longitudinal direction.

Each individual actuation device can have an allocated annular groove or respective recess which extends as a ring about the longitudinal direction of the respective plastic container.

The present inventive concepts is furthermore oriented at a method for cleaning and/or sterilizing plastic preforms. The plastic preforms are here transported along a predefined path. During this transport, an interior of the plastic preforms is actuated upon by a flowable and in particular gaseous sterilization agent from a plurality of actuation devices. According to embodiments of the inventive concepts, the flowable medium is introduced into the plastic preforms at a predefined angle different from 0° in relation to the longitudinal direction thereof, and/or the longitudinal directions of the actuation devices are arranged offset in relation to the longitudinal direction of the plastic preforms during actuation.

In relation to the method, the actuation of the interiors of the plastic preforms is not carried out in the obvious manner, centrally to the longitudinal direction of the plastic preforms, but is modified with respect thereto. Advantageously, the flowable sterilization agent is injected at a predefined angle to the longitudinal direction. Also, the actuation devices are arranged offset to the longitudinal directions of the plastic preforms.

Advantageously, at least a portion of the actuation device from which the sterilization agent emerges is arranged angled in relation to the longitudinal direction of the plastic preforms in the manner described herein, such that the outlet direction defined by this portion has the above-mentioned angle in relation to the longitudinal direction of the plastic preforms. Advantageously, the actuation devices move together with the plastic preforms.

Advantageously, with the method described herein, a pre-sterilization of the plastic containers or respectively plastic preforms is carried out. Advantageously, following the sterilization described here, the plastic preforms are molded into plastic containers by means of an apparatus for molding plastic preforms into plastic containers, and preferably the resulting plastic containers are then sterilized once again. This additional sterilization can also take place by a flowable sterilization agent.

As stated above, the injection direction of the sterilization agent can also include a component in a direction opposite the transport direction of the plastic preforms.

Advantageously, between the mouth edges of the plastic preforms and a carrier on which the actuation devices are arranged, a flow is generated by the movement of the plastic preforms, which also ensures a flow in the plastic preforms which causes at least large parts of the inner wall of the plastic preforms to be actuated upon with the gaseous sterilization agent. It is therefore possible for the plastic preforms to be rotated about their own longitudinal direction during sterilization.

Advantageously, the plastic preforms are held in the region of their mouthpiece, above the carrier ring during sterilization. The carrier ring is in particular a ring which is formed peripherally below the thread of the plastic container and protrudes in a radial direction. This ring serves for the transport and delivery of the plastic containers or respectively preforms. In a further advantageous method, the plastic preforms are moved at least partly along a circular transport path.

FIG. 1 shows a partial view of an apparatus 1 for sterilizing plastic preforms 10, in accordance with some embodiments. Each preforms 10 can extend in a longitudinal direction, for example, along a symmetry axis L. Each plastic preform 10 has a mouth portion 10a which has a larger cross-section than a base body of the plastic preform 10, and also has a thread 10b. A carrier ring 10c is provided below the thread 10b of the plastic preform 10. A holding device 22 holds the plastic preform 10 in a region of its mouth 10a, for example, at a region below the carrier ring 10c. A carrier 2 on which the plastic preform 10 is arranged during sterilization. This carrier 2 can preferably include a carrier wheel. The plastic preforms 10 can move in a transport direction P.

Above the mouths of the plastic preforms 10 an actuation device 4 is provided, which is actuated at an interior of the plastic preforms 10 with a sterilization agent. The actuation device 4 can be attached to a carrier 38 by one or more fixing devices 48, for example screws. In turn, the carrier 38 can itself move together with the transport device 2 so that the actuation device 4 is always arranged in the position shown above the plastic preforms 10. An actuation is possible in other orientations of the plastic preforms 10, for example, rotated preforms 10.

An actuation device 4 can extend in a longitudinal direction LB. A channel 42 via which the sterilization agent is supplied can also extend in the longitudinal direction LB. The channel 42 is formed in the interior of a base body 46 of the actuation device 4, or a respective nozzle device 4. A nozzle device 44 can be provided via which the sterilization agent reaches the interior of the plastic preforms 10. The nozzle device 44 can be arranged at an angle $\alpha$ relative to the longitudinal direction L of the plastic preforms 10. This longitudinal direction L is here also a vertical direction.

A gap 8 can be between the carrier 38 and in particular between an outlet opening from the actuation device 4 or respectively nozzle device 44 and the upper mouth edge of the plastic preforms 10. The nozzle device 44 can protrude downward beyond the carrier 38, since the plastic preforms 10 are transported together with the actuation devices 4. The gap 8 thus extends in a horizontal plane.

Thus, it is evident that the direction of injection of the sterilization agent is on the one hand at an angle $\alpha$ to the longitudinal direction L, i.e., also obliquely in relation to the transport direction of the plastic preform 10. On the other hand, the longitudinal direction LB of the actuation device 4 is offset towards the rear in relation to the longitudinal direction L of the plastic preform 10, i.e. opposite the transport direction P. The offset here results from the distance d between the parallel longitudinal directions L and LB.

Figure 2:
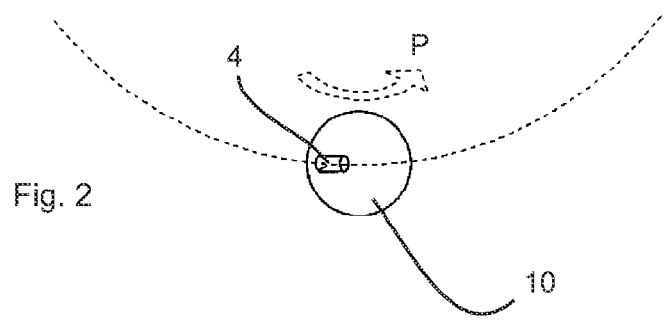
FIG. 2 is a diagrammatic depiction illustrating the injection direction of the actuation device, in accordance with some embodiments.

FIG. 2 shows a diagrammatic view illustrating the arrangement of an actuation device, in accordance with some embodiments. From this view it is also evident that the actuation device 4 is firstly offset in relation to the centre of the plastic preform 10 and hence also in relation to its longitudinal direction, opposite to the transport direction P. FIG. 2 also shows the oblique position of the actuation device 4 or, although not shown, the respectively nozzle portion 44, and the resulting oblique direction of the sterilization agent. It is evident from FIG. 2 that the plastic preforms 10 are transported along a circular transport path.

Figure 3:
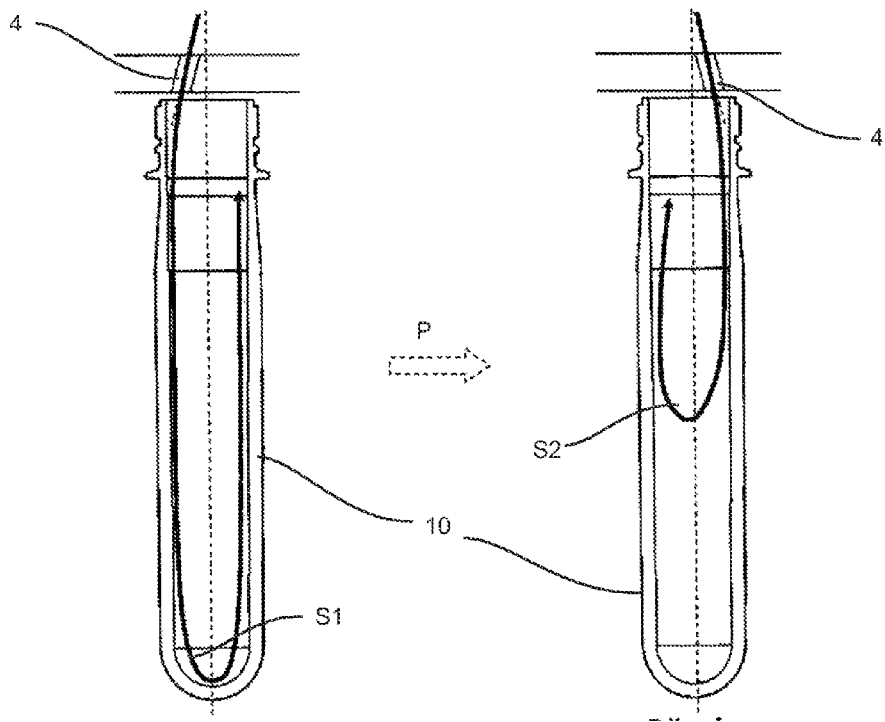
FIG. 3 are illustrations of a comparison between different injections, in accordance with some embodiments.

FIG. 3 are illustrations of a comparison between different injections, in accordance with some embodiments. During sterilization, both a plastic preform 10 and a nozzle, for example, nozzle 44 described herein, are moved in a transport direction. To minimize the disruptive influence of the resulting gap flow, as stated above, the nozzle is set at the angle $\alpha$ relative to the transport direction. The nozzle can also be offset along the transport direction eccentrically in relation to the center of the nozzle. To distribute the process gas or respectively sterilization agent onto the entire inner surface of the plastic preform as quickly as possible, the flow impacts on the inner wall of the plastic preform via the shortest route. Thus, at a boundary layer, a laminar flow occurs, which can quickly extend at the inner wall as far as the base of the plastic preform. This is illustrated in the left-hand depiction of FIG. 3, as shown by the flow course S1 of the sterilization agent according to the arrangement of the actuation device, in accordance with the inventive concepts.

When the nozzle is angled obliquely or otherwise slanted relative to the transport direction, the resulting gap flow supports the deposition of the process gas flow. When angled in the transport direction, the gap flow counters the deposition, as illustrated by the depiction in the right-hand side of FIG. 3 (flow course S2). In this case, the process gas flow becomes increasingly turbulent and therefore smaller proportions of the sterilization agent are deposited on the base of the plastic preform 10. To optimize the system, the eccentricity can be formed adjustably, for adaptation to different mouthpiece parameters and/or station power levels.

Figure 4:
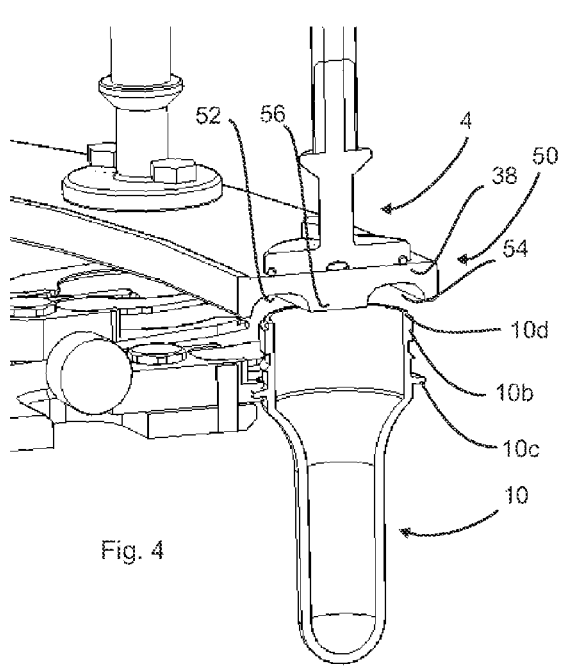
FIG. 4 is a view of an apparatus according to the inventive concepts with a deflection device for deflecting the flow emerging from the container onto the outer region of the plastic container, in accordance with some embodiments.

FIG. 4 shows another apparatus for sterilizing containers. A deflection device 50 is provided which deflects the sterilization agent emerging from one or more containers onto an outer surface of a container 10, in particular a threaded region 10b of the container 10.

Two grooves or recesses 52, 54 are arranged in the carrier 38 in its side 38a facing a container 10. A gaseous medium emerging from the container is deflected by these grooves and thus reaches the thread 10b of the plastic containers. The two grooves 52, 54 can extend beyond the mouth edge 10d of the plastic container.

Figure 5:
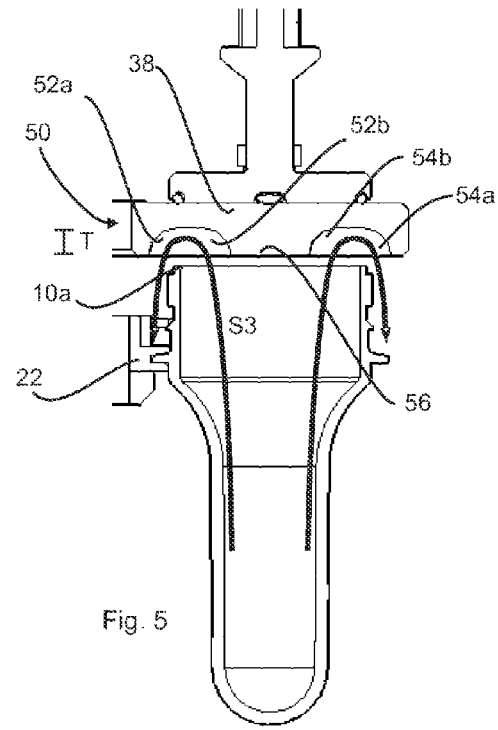
FIG. 5 is a view of the deflection device shown in FIG. 4.

FIG. 5 shows a cross-section view of the deflection device 50 of FIG. 4. It is evident that the respective radially larger regions 52b, 54b of the two grooves 52, 54 lie radially inside the container 10 or respectively its mouth cross-section, and that the respective radially smaller regions 52a, 54a lie radially outside the container 10. In this way a relatively large proportion of sterilization agent can be "captured" and deflected. A correspondingly targeted deflection can be achieved by the relatively small radial proportion 52b, 54b. In cross-section, the two recesses preferably have a semi-ellipsoid form. In the embodiment regarding the grooves 52, 54 described herein, a plurality of plastic preforms can be treated, each having different mouth diameters, using the deflection device 50. The two grooves 52, 54 can each extend beyond a mouth edge 10d of the plastic containers 10 in a radial direction thereof.

Thus the two radially offset grooves 52, 54 improve the disinfection of the outer surface of the plastic container 10. In the embodiment shown here, the two grooves 52, 54 extend as a ring along the carrier 38. Between the two grooves 52, 54 is provided a protrusion 56 which protrudes in the direction of the mouth of the plastic container (illustrated downward). The respective nozzles, through which the sterilization agent is supplied to the plastic preform, are located in this protrusion.

Preferably, the recesses have a maximum depth T between 2 and 10 mm. The flow course S3 of the sterilization agent emerging again from the plastic container or respective plastic preform.

The applicant reserves the right to claim all features disclosed in the application documents as being essential to the inventive concepts where novel individually or in combination in relation to the prior art.

The invention claimed is:

1. An apparatus for sterilizing plastic preforms, comprising:
 a transport device that transports the plastic preforms along a predefined transport path, each plastic preform extending in a longitudinal direction;
 a plurality of actuation devices, each actuation device inputting a flowable medium into interiors of the plastic preforms, respectively, wherein the actuation devices travel with the plastic preforms in a transport direction along the transport device, and wherein the actuation devices inject the flowable medium into the plastic preforms at a predefined angle α and a longitudinal direction of the actuation devices is offset eccentrically from a longitudinal direction of the plastic preforms by a predetermined distance, wherein an actuation device of the actuation devices is above a mouth of a preform of the plastic preforms, which provides a sterilization agent to an interior of the preform, and wherein the apparatus further comprises a plurality of fixing devices that attaches the actuation device to a carrier; and
 the carrier having a nozzle section fully protruding through the carrier in a direction being inclined towards the longitudinal direction of the plastic preforms, wherein an aperture of the actuation device is mounted in the longitudinal direction above the carrier so that the sterilizing medium can pass from the actuation device through the nozzle section and into the interior of the preform.

2. The apparatus of claim 1, wherein the actuation devices are arranged such that they inject the flowable medium into the plastic preforms at a predefined angle α that is different from 0° along which the longitudinal direction of the plastic preforms extend, such that a direction of injection has a component which is oriented opposite to the transport direction of the plastic preforms.

3. The apparatus according to claim 2, wherein the distance between the longitudinal direction of the plastic preforms and the longitudinal direction of the actuation devices is between 2 mm and 12 mm.

4. The apparatus according to claim 2, wherein the distance between the longitudinal direction of the plastic preforms and the longitudinal direction of the actuation devices is between 4 mm and 10 mm.

5. The apparatus according to claim 2, wherein the distance between the longitudinal direction of the plastic preforms and the longitudinal direction of the actuation devices is between 5 mm and 9 mm.

6. The apparatus according to claim 1, wherein the longitudinal direction of an actuation device of the actuation devices in a direction of movement of the plastic preforms is offset in relation to the longitudinal directions of the plastic preforms with respect to the transport direction of the plastic preforms.

7. The apparatus according to claim 1, further comprising a gap between mouths of the plastic preforms and the actuation devices, the gap extending in the transport direction of the plastic preforms.

8. The apparatus according to claim 1, wherein the actuation devices are arranged on a carrier.

9. The apparatus according to claim 1, wherein the predefined angle α is between 5° and 50°.

10. The apparatus according to claim 1, wherein the predefined angle α is between 10° and 30°.

11. The apparatus according to claim 1, wherein the predefined angle α is between 10° and 20°.

12. The apparatus according to claim 1, wherein the predefined angle α is between 12° and 18°.

13. The apparatus according to claim 1, wherein at least one of the predefined angle, the offset between the longitudinal direction of the plastic preforms and longitudinal directions of the actuation devices, or a height of the gap between the plastic preforms and the actuation device is adjustable.

14. The apparatus according to claim 1, further comprising a deflection device which deflects a sterilization agent emerging from a plastic container of the plastic preforms onto an outer region of the plastic container.

15. The apparatus according to claim 1; wherein the carrier is arranged adjacent to the mouth of the plastic preforms, wherein the carrier has at least one recess on a mouth of a plastic container of the plastic preforms, wherein the recess extends beyond a mouth edge of the plastic container in a radial direction thereof.

16. The apparatus according to claim 15, wherein the sterilization agent emerging from the plastic container is deflected by at least one recess of the carrier onto an outer face of a thread of the plastic container for sterilization.

17. The apparatus according to claim 16, wherein the at least one recess has a curved profile which causes a corresponding deflection of a sterilization medium.

18. The apparatus according to claim 7, wherein the actuation devices are arranged to be spaced apart from edges of the mouths of the plastic preforms.

19. The apparatus according to claim 1, wherein the plastic preforms are rotated about their longitudinal direction during sterilization.

20. The apparatus according to claim 1, wherein during sterilization of the plastic preforms, each actuation device is arranged at a precisely defined position in relation to the plastic preform or a holding device of the plastic preform allocated to the actuation device, and wherein the position does not change during sterilization of the plastic preforms.

21. The apparatus of claim 1, wherein the flowable medium includes a gaseous sterilization agent.

22. The apparatus of claim 21, wherein the actuation has a longitudinal direction, and a channel has a longitudinal direction via which the sterilization agent is supplied, and wherein the channel is formed in the interior of a base body of the actuation device or a respective nozzle device.

23. The apparatus of claim 1, wherein the carrier can move together with the transport device so that the actuation device is always arranged in a position above the plastic preforms.

24. The apparatus of claim 1, wherein the angle of the nozzle section is tangential to, or at an acute direction relative to, the longitudinal direction.

25. The apparatus of claim 1, wherein the nozzle section is fully integrated into the carrier.

* * * * *